(12) United States Patent
Stites et al.

(10) Patent No.: US 8,288,594 B2
(45) Date of Patent: Oct. 16, 2012

(54) SELECTIVE PROCESS FOR CONVERSION OF SYNGAS TO ETHANOL

(75) Inventors: Ronald C. Stites, Brighton, CO (US);
Shakeel Tirmizi, Matawan, NJ (US);
Jerrod Hohman, Superior, CO (US);
Stephen Deutch, Broomfield, CO (US)

(73) Assignee: Albemarle Corporation, Baton Rouge, LA (US)

( * ) Notice: Subject to any disclaimer, the term of this patent is extended or adjusted under 35 U.S.C. 154(b) by 142 days.

(21) Appl. No.: 12/951,296

(22) Filed: Nov. 22, 2010

(65) Prior Publication Data
US 2011/0124927 A1    May 26, 2011

Related U.S. Application Data

(60) Provisional application No. 61/264,211, filed on Nov. 24, 2009.

(51) Int. Cl.
*C07C 29/149* (2006.01)
*C07C 27/04* (2006.01)

(52) U.S. Cl. .......................... 568/885; 568/876; 568/884

(58) Field of Classification Search .................. 568/885, 568/876, 884
See application file for complete search history.

(56) References Cited

U.S. PATENT DOCUMENTS

| | | | | |
|---|---|---|---|---|
| 3,326,956 A | * | 6/1967 | Davies et al. ................. | 518/713 |
| 4,831,060 A | * | 5/1989 | Stevens et al. ............... | 518/714 |

* cited by examiner

*Primary Examiner* — Elvis O Price
(74) *Attorney, Agent, or Firm* — Jeremy J. Kliebert; Marcy M. Hoefling; James A. Jubinsky

(57) ABSTRACT

The present invention provides processes for selectively producing ethanol from syngas. In some variations, the process comprises converting biomass-derived syngas to dimethyl ether, carbonylating the dimethyl ether to methyl acetate, hydrogenating the methyl acetate to methanol and ethanol, and recovering the ethanol product. The methanol is preferably recycled by converting to hydrogen and carbon monoxide for introduction back into the process at distinct points. In certain variations of this invention, fresh syngas feed is introduced downstream of the first unit operation in the sequence. High yields of ethanol from biomass can be achieved according to the disclosed processes.

20 Claims, 2 Drawing Sheets

SELECTIVE PROCESS FOR CONVERSION OF SYNGAS TO ETHANOL

FIELD OF THE INVENTION

The present invention generally relates to processes for the conversion of synthesis gas into renewable liquid fuels, including ethanol.

BACKGROUND OF THE INVENTION

Synthesis gas, which is also known as syngas, is a mixture of gases comprising carbon monoxide (CO) and hydrogen ($H_2$). Generally, syngas may be produced from any carbonaceous material. In particular, biomass such as agricultural wastes, forest products, grasses, and other cellulosic material may be converted to syngas.

Syngas is a platform intermediate in the chemical and biorefining industries and has a vast number of uses. Syngas can be converted into alkanes, olefins, oxygenates, and alcohols such as ethanol. These chemicals can be blended into, or used directly as, diesel fuel, gasoline, and other liquid fuels. Syngas can also be directly combusted to produce heat and power. The substitution of alcohols and/or derivatives of alcohols in place of petroleum-based fuels and fuel additives can be particularly environmentally friendly when the alcohols are produced from feed materials other than fossil fuels.

In recent years, considerable research has been devoted to providing alternative sources and manufacturing routes for liquid hydrocarbon fuels in recognition of the fact that petroleum is a non-renewable resource and that petroleum-based fuels such as gasoline and distillate will ultimately become more expensive.

Ethanol is a commercially viable liquid transportation biofuel today. Catalytic approaches for converting syngas to ethanol typically convert syngas to methanol which is then converted to ethanol and other alcohols. One of the most significant economic challenges to date has been the poor carbon selectivities to ethanol.

Other challenges in catalytically converting syngas into ethanol include the cost and availability of suitable catalysts, catalyst sensitivity to small amounts of sulfur and nitrogen, requirements for relatively high $H_2$/CO feed ratios, and the generation of low-value co-products.

It is known that methanol can be converted into dimethyl ether (DME). Alternatively, syngas can be converted directly into DME by mixed catalysts with activities for generating methanol from syngas and for dehydrating methanol to DME. The DME can be carbonylated to produce methyl acetate, which can be hydrogenated to produce methanol and ethanol. The methanol can be recycled so that ethanol is the primary product. While this process is generally disclosed in the art, there remains a need for new process variations that allow for better overall economics—including capital-cost reduction, reduced process complexity, operating flexibility, and co-product potential.

What are desired, in view of the art and various commercial issues, are improved process configurations and apparatus for conversion of syngas (e.g., from biomass) and/or methanol into ethanol through DME as an intermediate.

SUMMARY OF THE INVENTION

In some variations, this invention provides a process for producing ethanol from syngas, the process comprising:
(a) providing syngas having an input $H_2$/CO ratio;
(b) converting a portion of the syngas to dimethyl ether;
(c) carbonylating at least some of the dimethyl ether to methyl acetate;
(d) hydrogenating at least some of the methyl acetate to methanol and ethanol;
(e) converting at least some of the methanol from step (d) to hydrogen and carbon monoxide;
(f) feeding the carbon monoxide generated in step (e) back to step (c);
(g) feeding the hydrogen generated in step (e) back to step (d); and
(h) recovering the ethanol.

The syngas is derived from biomass, in some embodiments. The input $H_2$/CO ratio can be selected from about 0.6 to about 1.4, such as about 0.8 to about 1.2, or about 0.9 to about 1.1.

In some embodiments, step (c) further comprises a $CO_2$ purge. In some embodiments, methanol and ethanol are separated by distillation and the methanol is recycled. The methanol can be recycled directly to step (b). More preferably, step (e) comprises catalytically converting the methanol to hydrogen and carbon monoxide and then separating the hydrogen from the carbon monoxide. Alternatively, or additionally, step (e) comprises a two-step methyl formate process to generate separate hydrogen and carbon monoxide streams.

Other variations of the invention provide a process for producing ethanol from syngas, the process comprising:
(a) providing fresh syngas having an input $H_2$/CO ratio;
(b) providing a recycle stream comprising syngas components and methanol;
(c) converting a portion of the recycle stream to dimethyl ether;
(d) carbonylating at least some of the dimethyl ether to methyl acetate;
(e) introducing the fresh syngas and the methyl acetate to a unit for hydrogenating at least some of the methyl acetate to methanol and ethanol;
(f) separating the ethanol from the recycle stream; and
(g) recovering the ethanol.

The syngas is derived from biomass, in some embodiments. The input $H_2$/CO ratio can be selected from about 0.6 to about 1.4, such as about 0.8 to about 1.2, or about 0.9 to about 1.1.

In some embodiments, step (d) further comprises a $CO_2$ purge. In some embodiments, methanol and ethanol are separated by distillation and the methanol is recycled. A portion of the methanol can be recycled directly to step (c). In certain embodiments, some of the methanol is catalytically converted to hydrogen and carbon monoxide for introducing to step (e).

Various co-products may be recovered. For example, in some embodiments one or more of methanol, dimethyl ether, methyl acetate, syngas, hydrogen, carbon monoxide, carbon dioxide, and electricity are recovered for commercial purposes.

In a particular embodiment, a process for producing ethanol from biomass comprises the steps of:
(a) converting biomass into syngas having an $H_2$/CO ratio from 0.6 to 1.4;
(b) converting the syngas to dimethyl ether;
(c) carbonylating the dimethyl ether to methyl acetate;
(d) hydrogenating the methyl acetate to methanol and ethanol;
(e) converting the methanol to hydrogen and carbon monoxide;
(f) feeding the carbon monoxide generated in step (e) back to step (c);

(g) feeding the hydrogen generated in step (e) back to step (d); and (h) recovering said ethanol.

The present invention includes apparatus capable of carrying out the disclosed processes. The present invention also includes compositions comprising ethanol produced in accordance with the disclosed processes.

Figure 1:
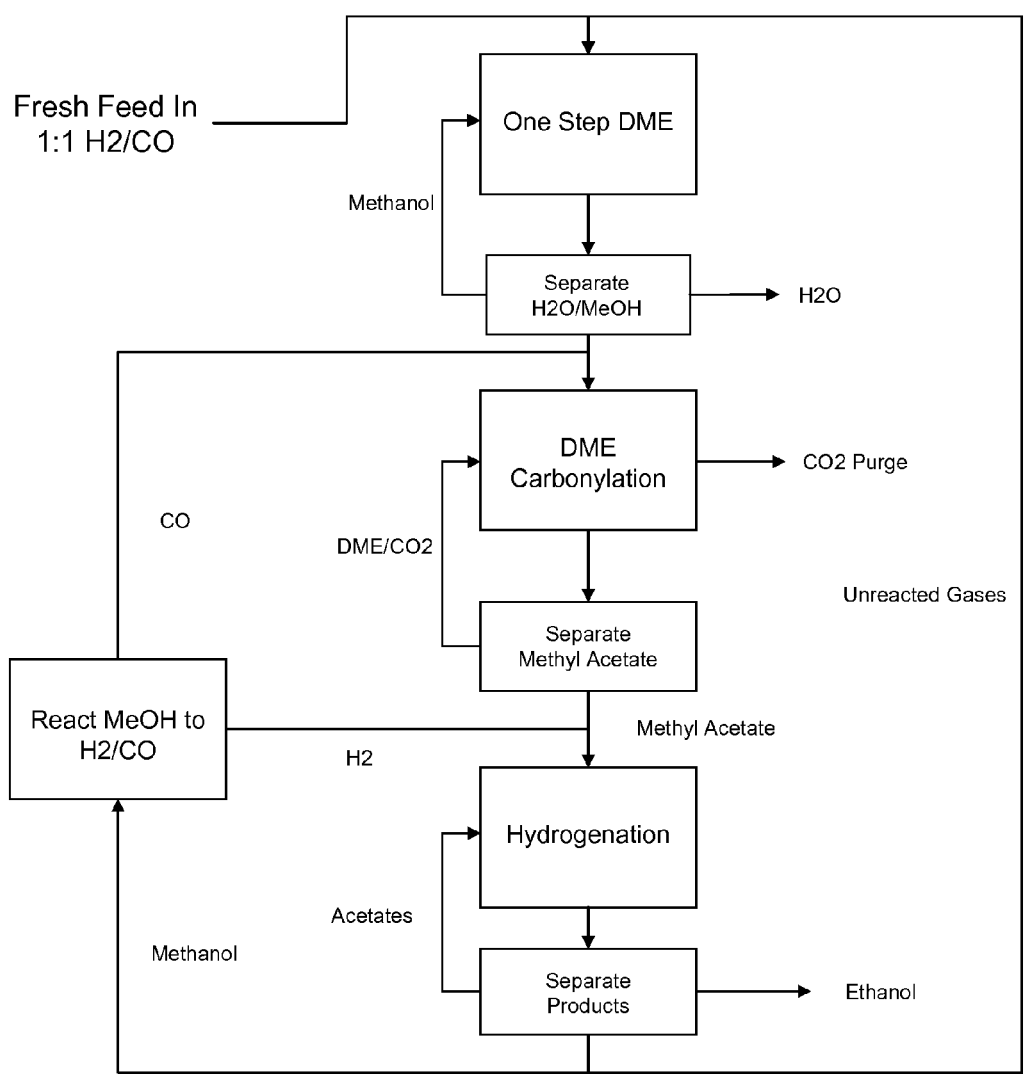
FIG. 1 depicts an exemplary process for selectively converting syngas into ethanol, according to certain variations of the invention.

These and other embodiments, features, and advantages of the present invention will become more apparent to those skilled in the art when taken with reference to the following detailed description of the invention in conjunction with the accompanying drawings.

DETAILED DESCRIPTION OF EMBODIMENTS OF THE INVENTION

Certain embodiments of the present invention will now be further described in more detail, in a manner that enables the claimed invention so that a person of ordinary skill in this art can make and use the present invention.

Unless otherwise indicated, all numbers expressing reaction conditions, stoichiometries, ratios, yields, and so forth used in the specification and claims are to be understood as being modified in all instances by the term "about." Accordingly, unless indicated to the contrary, the numerical parameters set forth in the following specification and attached claims are approximations that may vary depending at least upon the specific analytical technique. Any numerical value inherently contains certain errors necessarily resulting from the standard deviation found in its respective testing measurements.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs. If a definition set forth in this section is contrary to or otherwise inconsistent with a definition set forth in patents, published patent applications, and other publications that are herein incorporated by reference, the definition set forth in this specification prevails over the definition that is incorporated herein by reference.

Some variations of the invention relate to an integrated biorefinery capable of producing one or more liquid transportation fuels, including oxygenated fuels such as ethanol, methanol, and dimethyl ether (DME), from syngas. DME itself is a suitable liquid fuel (e.g., as a diesel fuel), may be combined with other liquids, may be chemically converted into gasoline components, or may be converted into ethanol according to methods disclosed herein.

Syngas can be provided or produced by any known means, such as by one or more of gasification, pyrolysis, devolatilization, steam reforming, and partial oxidation of one or more feedstocks recited herein. In some embodiments, syngas is produced by the methods taught in U.S. patent application Ser. No. 12/166,167, entitled "METHODS AND APPARATUS FOR PRODUCING SYNGAS," filed Jul. 1, 2008, whose assignee is the same as the assignee of this patent application, and which is hereby incorporated by reference herein.

Syngas is preferably, but not necessarily, produced from biomass. Other sources of syngas include, for example, natural gas, coal, crude oil, and any other carbonaceous material. In some embodiments, the syngas provided or generated for methods of this invention is produced from one or more carbon-containing feedstocks selected from timber harvesting residues, softwood chips, hardwood chips, tree branches, tree stumps, leaves, bark, sawdust, paper pulp, corn stover, wheat straw, rice straw, sugarcane bagasse, switchgrass, miscanthus, animal manure, municipal solid waste, municipal sewage, commercial waste, used tires, grape pumice, almond shells, pecan shells, coconut shells, coffee grounds, grass pellets, hay pellets, wood pellets, cardboard, paper, plastic, rubber, cloth, coal, lignite, coke, lignin, and/or petroleum. Mixtures of any of these feedstocks may be used.

Production of syngas from biomass typically generates syngas with a $H_2/CO$ ratio of about 1, such as about 0.6, 0.7, 0.8, 0.9, 1.0, 1.1, 1.2, 1.3, or 1.4. Cellulosic biomass can be represented by the formula $C_n(H_2O)_n$ wherein n is 5 or 6 for repeat units within the cellulosic material. Therefore, the units of cellulosic biomass contain C, H, and O atoms collectively having a $H_2/CO$ ratio of one.

The $H_2/CO$ ratio of syngas derived from thermochemical conversion of biomass (or any other feedstock) will depend in part on whether steam or oxygen is employed. Generally speaking, when oxygen is employed the ratio will be lower due to partial oxidation of carbon molecules to CO. Although large amounts of steam can be utilized to drive $H_2/CO$ ratios closer to 2 or more, such steam reforming of biomass can add significant cost to the process.

Preferably, processes are designed to be capable of utilizing syngas having a $H_2/CO$ ratio of about 1. More preferably, according to some variations of the present invention, process steps and catalysts are selected to optimize the process when feeding syngas having $H_2/CO$ ratios of about 0.6-1.4, preferably about 0.8-1.2, and more preferably about 0.9-1.1, including approximately 1.0. It is recognized that a single-step unit converting syngas to DME ($CH_3OCH_3$) stoichiometrically consumes syngas in a 1:1 ratio of hydrogen and carbon monoxide, according to $$3H_2 + 3CO \rightarrow CH_3OCH_3 + CO_2$$

In some variations, this reaction is carried out in a slurry reactor (as described, for example, in Shikada et al., *Natural Gas Conversion V*, vol. 119, pp. 515-520, 1998). Mechanistically, it is believed (without being limited to any particular hypothesis) that this reaction proceeds through methanol as an intermediate, with the methanol dehydrating to dimethyl ether. Thus, preferred catalyst systems for this step include both methanol-synthesis activity (e.g., Cu/ZnO) and methanol-dehydration activity (e.g., solid acids).

Dimethyl ether can be further reacted with carbon monoxide to produce methyl acetate ($CH_3COOCH_3$) according to $$CH_3COCH_3 + CO \rightarrow CH_3COOCH_3$$

This reaction step can be catalyzed by, for example, H-mordenite (as described in Cheung et al., *Angewandte Chemie International Edition English*, vol. 45, pp. 1617-1620, 2006, for example).

Methyl acetate can be reacted with hydrogen to produce methanol and ethanol (without any substantial $H_2O$ or $CO_2$ formation) according to $$CH_3COOCH_3 + 2H_2 \rightarrow CH_3CH_2OH + CH_3OH$$

There are several commercially available Cu/ZnO-based catalysts that can accomplish this reduction. Methanol and ethanol can be separated using known methods, such as distillation. The methanol can be recycled to the reaction system as further described below. Alternatively, or additionally, methanol can be captured as a co-product.

When the above-described three reactions are conducted, the overall reaction produces one mole of ethanol and one mole of carbon dioxide from three moles of hydrogen plus three moles of carbon monoxide:

$$3H_2 + 3CO \rightarrow CH_3CH_2OH + CO_2$$

In this scheme and in the absence of side reactions, two-thirds of the feed carbon atoms are directed to ethanol. This scheme is thus highly selective for ethanol.

Figure 2:
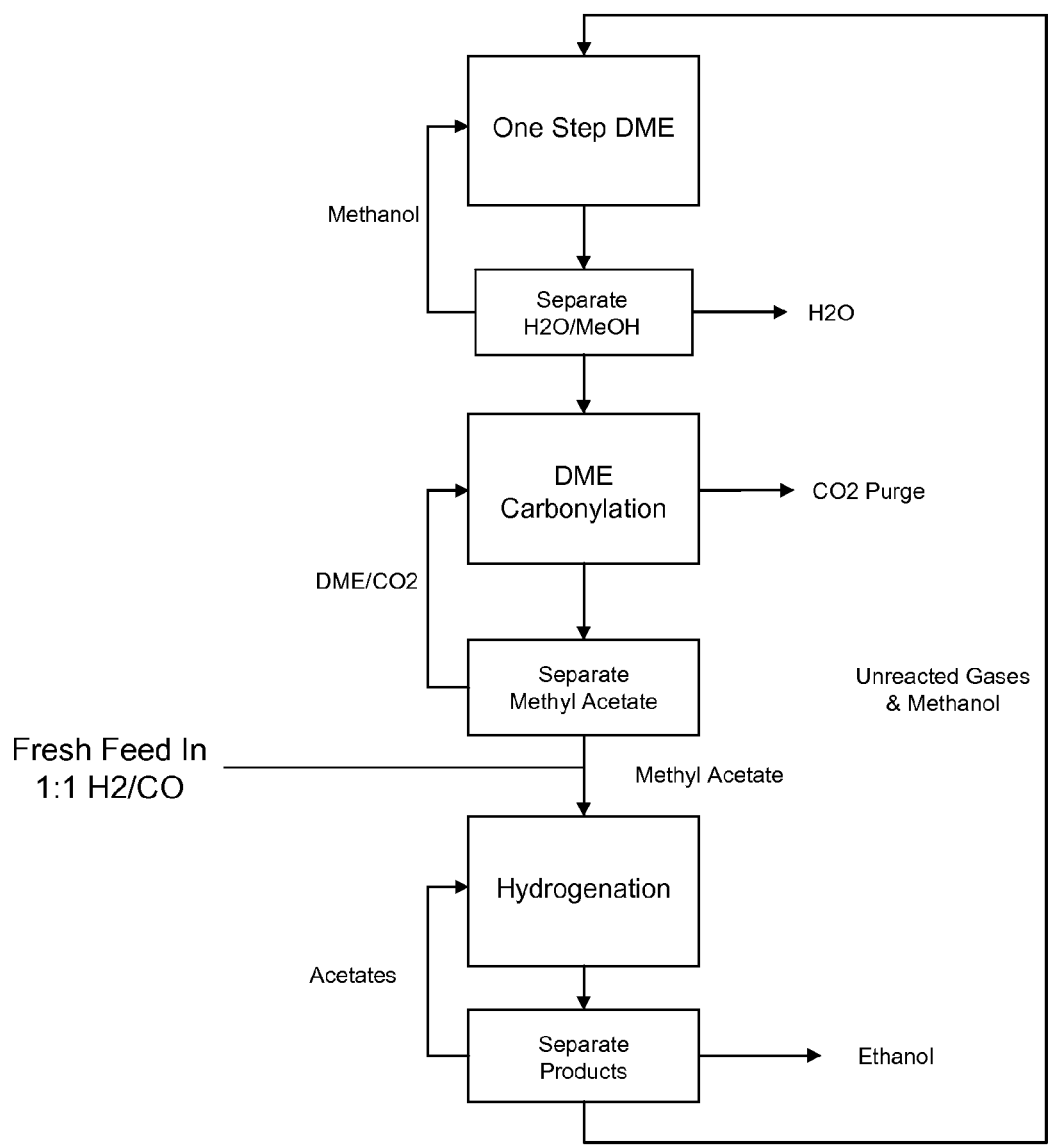
FIG. 2 depicts another exemplary process for selectively converting syngas into ethanol, according to other variations of the invention.

The present invention will now be further described by reference to the figures. This exemplary detailed description illustrates by way of example, not by way of limitation, the principles of the invention. In FIGS. 1 and 2, process block-flow diagrams are depicted for certain non-limiting variations of the invention.

FIG. 1 depicts one process configuration of the present invention. In FIG. 1, syngas is converted to DME by one-step synthesis, with removal of water formed in dehydration. The DME is then carbonylated to methyl acetate, with an optional purge of $CO_2$. The methyl acetate is hydrogenated to produce methanol and ethanol, which are substantially separated from each other. The ethanol product has low water content and can be sold directly or subjected to further purification, if desired. Methanol is recycled either directly or by converting it to syngas. Also, unreacted gases are recycled to the DME-synthesis reactor. Various optional internal recycle streams are included in FIG. 1.

In the variation of FIG. 1, the methanol is reacted to syngas components with the CO fed to the DME carbonylation step and the $H_2$ fed to the methyl acetate hydrogenation step. There are several options for this unit. Methanol can be converted to syngas by employing e.g. a Cu/Zn/$Al_2O_3$ catalyst, operating at conditions that favor the syngas side of the equilibrium ($CH_3OH \leftrightarrow 2H_2 + CO$), and separating the $H_2$ from the CO using known methods (such as membrane separation).

Alternatively, a two-step methyl formate process can be employed to generate separate $H_2$ and CO streams. For example, a two-step methyl formate process is described in Ikarashi, *Chemical Economy & Engineering Review*, vol. 12, no. 8, pp. 31-34, 1980. In some embodiments, methanol can be recycled directly to the first reactor (DME synthesis).

FIG. 2 depicts another process configuration of the present invention. This variation is premised, in part, on the realization that fresh syngas feed can be introduced into the methyl acetate hydrogenation step rather than into the DME-synthesis step. One advantage to this approach is the avoidance of complexity and cost associated with decomposing methanol to syngas.

In FIG. 2, DME is generated in a one-step synthesis unit as in FIG. 1, except that the feed is not fresh syngas. Instead, the feed comprises methanol and unreacted gases (including CO) exiting the ethanol-separation unit after methyl acetate hydrogenation. The DME is carbonylated to methyl acetate, with an optional purge of $CO_2$. The methyl acetate is hydrogenated (using $H_2$ from fresh syngas feed) to produce methanol and ethanol, which are substantially separated from each other. The ethanol product has low water content and can be sold directly or subjected to further purification, if desired.

It will be apparent to a skilled artisan that many variations and embodiments arise from the process configurations shown in FIGS. 1 and 2. For example, fresh syngas feed could be split into multiple streams, with a portion being fed to the DME-synthesis unit and a portion fed to the methyl acetate hydrogenation unit. Some of the methanol produced could be reacted to syngas, and some of the syngas combined with fresh syngas for introduction at various process points.

In some variations, syngas is produced or otherwise provided in a biorefinery. The syngas can be divided into a plurality of streams and fed to several unit operations. Syngas can be a fuel itself to provide internal process energy, or sold directly as a co-product, or converted into electricity for external sale. At least a portion of the syngas, in the context of the present invention, is converted to liquid fuels.

Biorefinery co-products that can be produced (along with ethanol as the primary product) in various embodiments of the invention include, but are by no means limited to, methanol, dimethyl ether, methyl acetate, syngas, hydrogen, carbon monoxide, carbon dioxide, and electricity. Biorefinery economic optimization may be carried out to adjust the production of co-products. As will be appreciated, various grades and purities for products and co-products are contemplated.

Final product mixes from a biorefinery may be optimized for maximum profitability and/or minimum carbon footprint, for example, by known techniques. Preferred embodiments of the invention can reduce overall energy intensity and/or reduce the number of processing steps to selectively produce ethanol from biomass.

The reaction temperature, pressure, catalyst, and residence time for each process step are each not regarded as critical, provided that overall conditions are suitable for a desired conversion. In some embodiments, conditions are optimized for one or more individual units. In other embodiments, overall process optimization is carried out.

With reference to FIGS. 1 and 2, each block is associated with a reactor or a separation unit. A "reactor" described herein may be any type of catalytic reactor suitable for the desired chemistry. A reactor may, for example, be a fixed-bed reactor. In some variations, a reactor comprises tubes filled with one or more catalysts. Syngas passing through the tubes undergoes catalyzed reactions to form alcohols or other products. A reactor can also be a fluidized bed or a slurry reactor, for example.

Each reactor can be engineered and operated in a wide variety of ways. Reactor operation can be continuous, semi-continuous, or batch. Operation that is substantially continuous and at steady state is preferable. The flow pattern can be substantially plug flow, substantially well-mixed, or a flow pattern between these extremes. The flow direction can be vertical-upflow, vertical-downflow, or horizontal. A vertical configuration can be preferable.

Any reactor used herein can in fact be a series or network of several reactors in various arrangements.

The catalyst phase can be a packed bed or a fluidized bed. The catalyst particles can be sized and configured such that the chemistry is, in some embodiments, mass-transfer-limited or kinetically limited. The catalyst can take the form of a powder, pellets, granules, beads, extrudates, and so on. When a catalyst support is optionally employed, the support may assume any physical form such as pellets, spheres, monolithic channels, etc.

Engineering optimization may also be conducted to achieve energy integration. For example, energy requirements for product separations can be reduced by combining portions of the product streams from individual processes into a single unit. Various levels of heat recovery can be employed to meet separation requirements. Many of the steps described herein are significantly exothermic and can supply much of the required process energy.

All publications, patents, and patent applications cited in this specification are incorporated herein by reference in their entirety as if each publication, patent, or patent application was specifically and individually put forth herein.

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims.

Any reference to a method step or process step as being carried out on a stream or component also includes the step being carried out on a portion, but not necessarily the entirety of, the stream or component. The remainder of the respective stream or component may be unprocessed, purged, recovered, fed to a different step or unit, reacted away, and so on.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially.

Therefore, to the extent that there are variations of the invention, which are within the spirit of the disclosure or equivalent to the inventions found in the appended claims, it is the intent that this patent will cover those variations as well. The present invention shall only be limited by what is claimed.

What is claimed is:

1. A process for producing ethanol from syngas, said process comprising:
    (a) providing syngas having an input $H_2/CO$ ratio;
    (b) converting a portion of said syngas to dimethyl ether;
    (c) carbonylating at least some of said dimethyl ether to methyl acetate;
    (d) hydrogenating at least some of said methyl acetate to methanol and ethanol;
    (e) converting at least some of said methanol from step (d) to hydrogen and carbon monoxide;
    (f) feeding said carbon monoxide generated in step (e) back to step (c);
    (g) feeding said hydrogen generated in step (e) back to step (d); and
    (h) recovering said ethanol.

2. The process of claim 1, wherein said syngas is derived from biomass.

3. The process of claim 1, wherein said input $H_2/CO$ ratio is selected from about 0.6 to about 1.4.

4. The process of claim 3, wherein said input $H_2/CO$ ratio is selected from about 0.8 to about 1.2.

5. The process of claim 3, wherein said input $H_2/CO$ ratio is selected from about 0.9 to about 1.1.

6. The process of claim 1, wherein step (c) further comprises a $CO_2$ purge.

7. The process of claim 1, wherein methanol and ethanol are separated by distillation.

8. The process of claim 1, further comprising recycling a portion of said methanol directly to step (b).

9. The process of claim 1, wherein step (e) comprises catalytically converting said methanol to hydrogen and carbon monoxide and then separating said hydrogen from said carbon monoxide.

10. The process of claim 1, wherein step (e) comprises a two-step methyl formate process to generate separate hydrogen and carbon monoxide streams.

11. A process for producing ethanol from syngas, said process comprising:
    (a) providing fresh syngas having an input $H_2/CO$ ratio;
    (b) providing a recycle stream comprising syngas components and methanol;
    (c) converting a portion of said recycle stream to dimethyl ether;
    (d) carbonylating at least some of said dimethyl ether to methyl acetate;
    (e) introducing said fresh syngas and said methyl acetate to a unit for hydrogenating at least some of said methyl acetate to methanol and ethanol;
    (f) separating said ethanol from said recycle stream; and
    (g) recovering said ethanol.

12. The process of claim 11, wherein said syngas is derived from biomass.

13. The process of claim 11, wherein said input $H_2/CO$ ratio is selected from about 0.6 to about 1.4.

14. The process of claim 13, wherein said input $H_2/CO$ ratio is selected from about 0.8 to about 1.2.

15. The process of claim 13, wherein said input $H_2/CO$ ratio is selected from about 0.9 to about 1.1.

16. The process of claim 11, wherein step (d) further comprises a $CO_2$ purge.

17. The process of claim 11, further comprising catalytically converting said methanol to hydrogen and carbon monoxide for introducing to step (e).

18. The process of claim 11, comprising a two-step methyl formate process to generate separate hydrogen and carbon monoxide streams.

19. The process of claim 11, further comprising recovering a co-product selected from the group consisting of methanol, dimethyl ether, methyl acetate, syngas, hydrogen, carbon monoxide, carbon dioxide, and electricity.

20. A process for producing ethanol from biomass, said process comprising:
    (a) converting biomass into syngas having an $H_2/CO$ ratio from 0.6 to 1.4;
    (b) converting said syngas to dimethyl ether;
    (c) carbonylating said dimethyl ether to methyl acetate;
    (d) hydrogenating said methyl acetate to methanol and ethanol;
    (e) converting said methanol to hydrogen and carbon monoxide;
    (f) feeding said carbon monoxide generated in step (e) back to step (c);
    (g) feeding said hydrogen generated in step (e) back to step (d); and
    (h) recovering said ethanol.

* * * * *